(12) United States Patent
Rich

(10) Patent No.: US 7,307,051 B2
(45) Date of Patent: Dec. 11, 2007

(54) COLOR CHANGING HAND SOAP COMPOSITION

(76) Inventor: Sarah Rich, 94 Fisher St., Westborough, MA (US) 01581

( * ) Notice: Subject to any disclaimer, the term of this patent is extended or adjusted under 35 U.S.C. 154(b) by 0 days.

(21) Appl. No.: 11/156,758

(22) Filed: Jun. 20, 2005

(65) Prior Publication Data
US 2005/0233918 A1 Oct. 20, 2005

Related U.S. Application Data

(62) Division of application No. 10/690,582, filed on Oct. 23, 2003, now abandoned.

(51) Int. Cl.
*C11D 3/20* (2006.01)
(52) U.S. Cl. .................. 510/138; 510/159; 510/463; 510/481; 510/509; 510/462
(58) Field of Classification Search .................. None
See application file for complete search history.

(56) References Cited

U.S. PATENT DOCUMENTS

| | | | |
|---|---|---|---|
| 4,610,589 | A | 9/1986 | Bredal |
| 4,896,144 | A | 1/1990 | Bogstad |
| 5,467,481 | A | 11/1995 | Srivastava |
| 5,771,925 | A | 6/1998 | Lewandowski |
| 5,793,653 | A | 8/1998 | Segal |
| 5,952,924 | A | 9/1999 | Evans et al. |
| 6,029,600 | A | 2/2000 | Davis |
| 6,278,372 | B1 | 8/2001 | Velasco, Jr. et al. |
| 6,403,543 | B1 * | 6/2002 | George ................... 510/147 |
| 6,426,701 | B1 | 7/2002 | Levy et al. |
| 6,428,799 | B1 * | 8/2002 | Cen et al. .................. 424/402 |
| 6,524,624 | B1 * | 2/2003 | Morelli et al. .............. 424/665 |
| 6,818,603 | B2 * | 11/2004 | Aleles et al. ............... 510/148 |
| 6,897,253 | B2 * | 5/2005 | Schmucker-Castner et al. .............. 524/291 |
| 6,899,893 | B2 * | 5/2005 | Tsuji et al. ................. 424/439 |
| 6,916,493 | B2 * | 7/2005 | Morelli et al. .............. 424/665 |

FOREIGN PATENT DOCUMENTS

FR 2805162 * 8/2001

OTHER PUBLICATIONS

G. Fundueanu et al., "Physico-Chemical Characterization of Ca-alginate Microparticles Produced With Different Methods", *Biomaterials*, vol. 20, pp. 1427-1435 (1999).

(Continued)

*Primary Examiner*—Necholus Ogden
(74) *Attorney, Agent, or Firm*—Fish & Richardson P.C.

(57) ABSTRACT

A composition can indicate whether hands have been washed for an approximate predetermined period of time. The composition includes a pH indicator and a delivery system. The delivery system contains a pH-altering compound. The delivery system is added to the pH indicator approximately when hand washing begins. A method of washing hands is also presented. The pH indicator is applied to the hands. The delivery system is applied to the hands approximately when hand washing begins. The pH indicator and delivery system are mixed. A system for washing hands is also presented. The system includes a pH indicator, a delivery system, and a dispenser that releases the pH indicator and delivery system to hands. The hands are washed until the pH indicator changes color.

2 Claims, 1 Drawing Sheet

OTHER PUBLICATIONS

R.S. Hermes et al., "Polymeric Alginate Films and Alginate Beads for the Controlled Delivery of Macromolecules", *Trends Biomater. Artif. Organs.*, vol. 15 (2) pp. 54-56 (2002).

M. L. Huguet, "Calcium Alginate Beads Coated With Chitosan: Effect of the Structure of Encapsulated Materials on Their Release", *Process Biochemistry*, vol. 31, No. 8, pp. 745-751 (1996).

Hand Washing, "Hand Washing", reprinted from http://healthlink.mcw.edu/article/955074416.html, printed on Dec. 16, 2003 (2 pages).

eLCOSH: An Employer's Guide to Skin Protection, "An Employer's Guide to Skin Protection", reprinted from http://www.cdc.gov/elcosh/docs/d0400/d000457/d000457.html, printed on Dec. 16, 2003 (32 pages).

Acids, "Acids, Bases and Neutralization", reprinted from http://oxygen.chem.uidaho.edu/tebchem111/lecture_content/printerfriendly/pfacidbase1.html, printed on Dec. 19, 2003 (3 pages).

Red cabbage pH indicator, "Red Cabbage Juice pH Indicator", reprinted from http://chemlern.chem.indiana.edu/demos/REDCABBA.HTM, printed on Dec. 16, 2003 (3 pages).

ICHC Chemistry Department, reprinted from http://chemistry.ichc.ro/print.php?sid=46, printed on Jan. 12, 2004 (2 pages).

How to Make Red Cabbage Juice pH Indicator-Acid Base Chemistry, "How to Make Red Cabbage pH Indicator" reprinted from http://chemistry.about.com/library/weekly/aa012803a.htm, printed Jan. 12, 2004 (4 pages).

Howstuffworks, "Where does the color come from in purple cabbage", reprinted from http://ww.howstuffworks.com/question439.htm/printable, printed Jan. 12, 2004.

S. Smith, Mom was right: Wash Your Hands, *The Boston Globe*, Oct. 1, 2002.

\* cited by examiner

COLOR CHANGING HAND SOAP COMPOSITION

This application is a divisional (and claims the benefit of priority under 35 USC 120) of U.S. application Ser. No. 10/690,582, filed Oct. 23, 2003, now abandoned. The disclosure of the prior application is considered part of (and is incorporated by reference in) the disclosure of this application.

TECHNICAL FIELD

This disclosure relates to the promotion of hygiene, and more particularly, to facilitating effective hand washing by indicating the duration of the hand-washing process.

BACKGROUND

Conventional soaps used for hand washing do not indicate whether the soap has been used for an appropriate amount of time for the process to be effective. As a result, hands are often washed for too short an amount of time for the process to be effective in cleansing hands. Properly washing your hands is one of the best ways to prevent infection and the spread of diseases. Doctors, nurses and other people who work in medical settings have to wash their hands frequently to avoid spreading infective agents between patients or to themselves. Those who prepare food must keep clean hands so they do not put germs into the food they are making. Also, childcare workers must wash their hands often so they do not make children sick. In addition to professionals whose hygiene is regulated, individuals should be conscious of the germs on their hands. Turning doorknobs, handling money and coughing may transfer bacteria and viruses to one's hands, which can then be spread to other people's hands or to your mouth and eyes and cause infection. Anyone who prepares food for others can infect others if his or her hands are not properly cleaned. Many of the diseases spread this way are more inconvenient than a simple cold. Some examples are the flu, hepatitis A and typhoid. See Wisconsin Department of Health and Family Services, "Hand Washing," available at <http://healthlink.mcw.edu/article/955074416.html>Aug. 29, 2002.

Approaches ensuring effective hand cleansing include antibacterial hand rubs. One drawback with such hand rubs is that such rubs may dry hands more than washing with soap. Another approach known involves applying a dye that glows under a black light to hands prior to washing hands, washing hands, then analyzing the effectiveness of the hand-washing process by examining the hands under a black light. In addition, some hospitals use electronic devices that alert an employee if the employee's hands were not effectively washed. Such approaches may be expensive and fail to achieve widespread use. The present disclosure may have one or more of the following advantages. The disclosure can be an easy, convenient, and inexpensive approach to facilitate effective hand washing.

SUMMARY

Hand washing compositions, methods, and systems are provided that can encourage proper hand washing as a way to promote good hygiene. In particular, the compositions, methods, and systems signal when hands have been washed for the recommended minimum amount of time, thereby contributing to an effective hand-washing process. The present disclosure can be used in a number of settings including, but not limited to, private homes, hospitals, childcare centers, nursing homes, schools, restaurants, airports, and food-preparation and food-processing establishments.

In one aspect, a composition that changes color during use includes a pH indicator and a delivery system. The delivery system can be added to the pH indicator approximately when hand washing begins. The delivery system contains a pH-altering compound. Upon washing the hands for an approximate predetermined period of time, the pH indicator changes color.

In another aspect, a method of washing hands for an approximate predetermined period of time includes the steps of applying a pH indicator to the hands and applying a delivery system to the hands. The delivery system contains a pH-altering compound and is added to the pH indicator approximately when hand washing begins. The pH indicator is mixed with the delivery system.

In one implementation, a flavin may be used as the pH indicator. The flavin may be a red cabbage isolate. The delivery system may also include alginate beads in addition to the pH-altering compound. In one example, the pH-altering compound may be a bicarbonate, such as $NaHCO_3$. The pH indicator may be present in a soap, either in a solid soap, liquid soap, or detergent.

In another aspect, a system for washing hands for an approximate predetermined amount of time includes a pH indicator, a delivery system, and a dispenser. The delivery system comprises a pH-altering compound. The dispenser releases the pH indicator and the delivery system to the user for washing hands. The hands are washed at least until the pH indicator changes color.

The dispenser may include at least two compartments. The first compartment can contain the pH indicator and the second compartment can contain the delivery system, which contains the pH-altering compound. The soap or detergent may be introduced separately or contained in either of those two compartments.

These and other implementations may have one or more of the following advantages. The implementations allow a determination of whether hands have been washed for at least an approximate predetermined period of time. The color change can signal that the appropriate period of time has lapsed. The predetermined period of time can be varied depending on the hand washing needs. The delivery system used can be altered to increase or decrease the time of release of the pH-altering compound. Alternatively, the concentration or composition of the pH-altering compound can be varied to increase or decrease the time of release.

The pH indicator can be added to a soap or detergent prior to hand washing or it can be added at the time of hand washing. The pH indicator utilized can be varied so that the color change occurs between different colors. Alternatively, the pH-altering compound can be varied, so that a given pH indicator changes to a different color with a different pH-altering compound.

The details of one or more implementations are set forth in the description below. Other features, objects, and advantages will be apparent from the description and from the claims.

DETAILED DESCRIPTION

Figure 1:
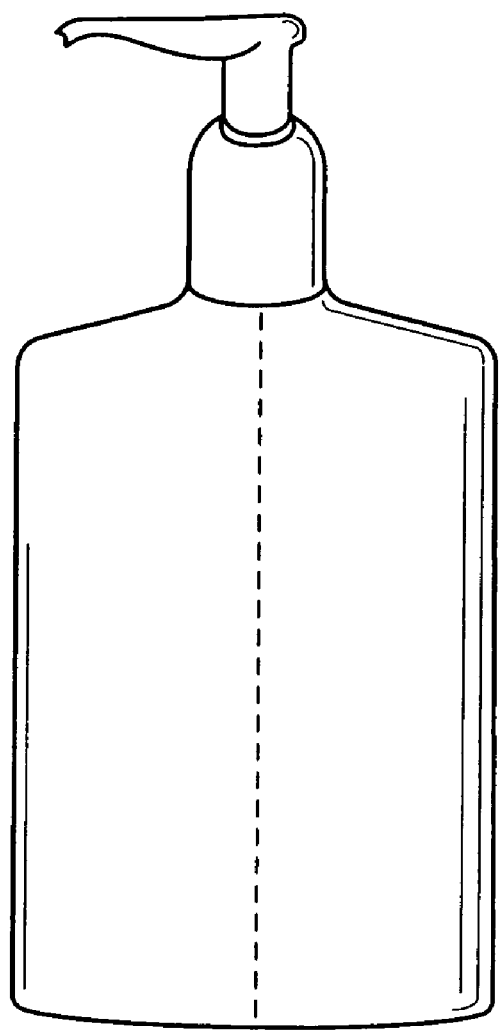
FIG. 1 is a front perspective view of a soap dispenser in accordance with one implementation. The dotted line represents the division between two compartments, one containing the pH indicator and the other containing the delivery system.
Figure 2:
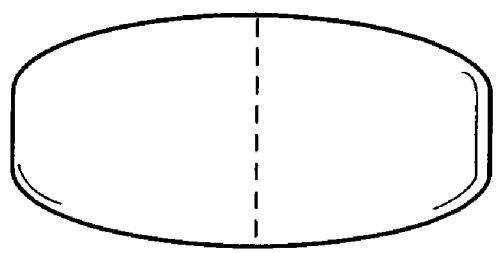
FIG. 2 is a view of a horizontal section of the dispenser illustrating the internal construction of the two-compartment implementation shown in FIG. 1.

In general, a composition for indicating whether hands have been washed for an approximate predetermined period of time includes a pH indicator that changes color as the pH of the environment surrounding the indicator changes. The pH indicator can be a naturally occurring substance. For example, the pH indicator can be an anthocyanin pigment molecule such as a flavin. Any pH indicator can be used, including, but not limited to, flavins and other anthocyanins. The pH indicator may be added to hands as hand washing begins or it may be present in a soap or a detergent.

In addition to the pH indicator, the composition also includes a delivery system that is added to the pH indicator approximately when hand washing begins. The delivery system contains a pH-altering compound. The pH-altering compound can either be an acidic or basic compound and can alter the pH of the environment surrounding the pH indicator, thereby causing the pH indicator to change color to reflect the change in the pH of the surrounding environment. Examples of pH-altering compounds include, but are not limited to, a bicarbonate such as sodium bicarbonate ($NaHCO_3$), washing soda ($Na_2CO_3$), citric acid ($C_6H_8O_7$), and acetic acid ($CH_3COOH$). Examples of pH-altering compounds such as citric acid can be found in lemon juice, while acetic acid can be found in vinegar. The pH-altering compound within the delivery system is released over time. Depending on the delivery system utilized, the release time can vary. The release time can also be predetermined, based on the delivery system used, the amount of the compound being released, and the concentration of the compound being released. The predetermined period of time can be greater than ten seconds, for example, fifteen seconds to two minutes.

Another aspect of the present disclosure is a method of washing hands for an approximate predetermined period of time, which is determined based on the time required to achieve effective hand washing and may vary in different circumstances. The recommended time is approximately twenty seconds for purposes of achieving clean hands in ordinary hygiene circumstances. However, the present disclosure can be modified to cause a more rapid or slower delivery of the pH-altering compound so that the color change occurs in a different amount of time to indicate a longer or shorter time period of hand washing. Medical professionals, for example, may need to wash their hands for a longer period of time to achieve even cleaner hands.

Calcium alginate beads can be used as a delivery system that releases its contents in the amount of time that is the minimum recommended time for effective hand washing. For example, alginate beads can be used to release sodium bicarbonate approximately twenty seconds after addition to the pH indicator. In a preferred implementation, the beads are approximately 1 mm to 3 mm in size.

At least two factors are known to affect the rate of release of substances from alginate beads. One factor is the size of the substance being released from the beads. Larger substances require more time to be released. A second factor is the concentration of the chemical in the solution that was mixed with the alginate solution. The higher the concentration, the more rapidly the substance is released. Mechanical forces, such as mixing and lathering, may also affect the release time. The beads may be created and then immediately mixed with a pH-altering compound to form the delivery system component of the composition, or they may alternatively be stored in a 150 mM NaCl, 1 mM $CaCl_2$ bead-storing solution.

In a further implementation of the composition the pH indicator used is flavin. Flavins can be obtained as an isolate from a variety of sources, including, but not limited to, red cabbage, apple skin, plums, poppies, cornflowers, and grapes. In one example, the flavin is a red cabbage isolate.

In a further implementation of the composition the delivery system comprises alginate beads and a pH-altering compound. The pH-altering compound may be $NaHCO_3$. In a further implementation of the composition, the pH indicator is present in soap, either in a solid soap or in a liquid soap. In a further implementation of the composition, the pH indicator is present in a soap or detergent.

As can be seen, many variations of the method are possible. For example, a stronger base can be used. A stronger base turns the flavin to a green or yellow color. Alternatively, an acidic pH-altering compound can be used. Such a pH-altering compound would cause the flavin to turn a deep red color.

Many systems may be used to practice the method with the claimed composition for color-changing soaps. As one example, a system may comprise a pH indicator, a delivery system that contains a pH-altering compound, and a dispenser that releases the pH indicator and delivery system to a user for washing hands. The hands are washed until the pH indicator changes color, at which time the color change indicates that the hands have been washed for an approximate predetermined amount of time.

The following is an example of an implementation of a system and is not intended to limit the system. The system comprises a dispenser possessing at least two chambers and a pump dispenser. One chamber contains a solution of alginate beads that contain sodium bicarbonate and a pH-altering compound, such as the pH-altering composition of Example 1. The other chamber contains a pH indicator such as the reddish flavin of Example 1. The pH indicator may be contained within a soap solution. To wash hands, the user compresses the pump to dispense appropriate amounts of the contents of the chambers onto the user's hands. The user then begins mixing the compositions by rubbing his or her hands together. After an approximate predetermined period of time lapses, the color of the pH indicator changes. For example, if flavin obtained from red cabbage is used, the pH indicator is initially red in color then changes color to purple when the approximate predetermined period of time has passed.

EXAMPLE 1

Color-Changing Composition

The following is an example of an implementation of the composition and is not intended to limit the composition. This example was directed to an approximate predetermined time of twenty seconds, which is the minimum recommended amount of time for effective hand washing.

a. pH-Indicator Composition

Flavin was isolated from red cabbage. Approximately two cups of boiling water were poured over approximately four cups of loosely packed cabbage leaves. The mixture was incubated at room temperature for approximately ten to fifteen minutes. The cabbage leaves were removed from the mixture. The remaining liquid, containing flavin, was boiled until the volume of the liquid was reduced to approximately one quarter of the starting volume of water. This flavin-containing pH indicator, which may be stored at approximately 4° C., was slightly acidic and had a reddish color. Next, a pH indicator-soap solution was made by adding 25% (by volume) water, 25% of the pH indicator solution, and 50% liquid hand soap. The liquid hand soap was slightly acidic, having a pH of approximately 6. The pH indicator soap solution was reddish in color.

b. Delivery System Composition

The pH-altering compound used in this example was sodium bicarbonate. The delivery system used was calcium alginate beads. To prepare the sodium bicarbonate-containing alginate beads, a 1.8% alginate solution was first made in sterile water. The solution was then filter-sterilized. Next, a near-saturated solution of sodium bicarbonate was prepared at approximately room temperature. The alginate and sodium bicarbonate solutions were combined in a volume ratio of approximately two parts alginate solution to approximately one part sodium bicarbonate solution. The resulting solution was mixed by inversion and monitored to ensure the absence of air bubbles. To create the sodium bicarbonate-containing alginate beads, the solution was added drop-wise by pipette into a 1.5% $CaCl_2$ solution. The resulting mixture was stirred with an automatic stirrer for approximately 5 minutes. The mixture was then left to stand for approximately 10 minutes. The resulting beads were rinsed three times in sterile water. The resulting beads were approximately 1 mm to approximately 3 mm in diameter.

c. Final Composition

The pH indicator composition was then mixed with the Delivery System Composition to create the color-changing hand soap composition.

EXAMPLE 2

Method of Washing Hands with Color Changing Soap

The following is an example of an implementation of the method and is not intended to limit of the method. The delivery system composition and pH-indicator containing composition from Example 1 were combined on the hands for washing. Specifically, about 2.5 mL of the pH indicator soap solution was applied to the hands. Approximately 1.25 mL of the sodium bicarbonate-containing alginate beads was then applied to the hands and the hands were washed by rubbing them together and mixing the two compositions. The color of the pH indicator changed from its starting reddish color to a purple color approximately twenty seconds after addition of the sodium bicarbonate-containing alginate beads.

A number of implementations have been described. Nevertheless, it will be understood that various modifications may be made without departing from the spirit and scope of the disclosure. Accordingly, other implementations are within the scope of the following claims.

What is claimed is:

1. A method of washing hands for an approximate minimum period of time predetermined to provide effective cleansing, the method comprising:
   a. providing a dual chamber dispenser containing a cleansing system comprising a first element and a second element formulated, upon mixing for the minimum period of time, to indicate passing of the minimum period of time by a change of color;
   b. applying to a user's hands from a first chamber of the dual chamber dispenser the first element of the cleansing system, the first element containing a pH indicator, where the pH indicator is red cabbage isolate;
   c. applying to the user's hands from a second chamber of the dual chamber dispenser the second element of the cleansing system comprising a soap or detergent and alginate beads containing a pH-altering compound; and
   d. performing hand washing motion of the user's hands for at least the minimum period of time, the hand washing motion mixing the cleansing system of the first element containing the pH indicator and the second element comprising soap or detergent and alginate beads containing the pH-altering compound and causing the cleansing system to change color, for indication of passing of the minimum period of time predetermined to provide effective cleansing.

2. The method of claim 1 wherein the pH-altering compound is a bicarbonate.

* * * * *